United States Patent [19]

Cox et al.

[11] Patent Number: 6,037,321
[45] Date of Patent: Mar. 14, 2000

[54] FUSION PROTEINS COMPRISING VASOACTIVE INTESTINAL PEPTIDE OR PACAP

[75] Inventors: Graham J.M. Cox; Jack Manns; Carolyn Weeks-Levy, all of Saskatoon, Canada

[73] Assignee: Biostar Inc., Saskatoon, Canada

[21] Appl. No.: 08/952,568

[22] PCT Filed: May 3, 1996

[86] PCT No.: PCT/CA96/00280

§ 371 Date: Oct. 29, 1997

§ 102(e) Date: Oct. 29, 1997

[87] PCT Pub. No.: WO96/34958

PCT Pub. Date: Nov. 7, 1996

Related U.S. Application Data

[63] Continuation-in-part of application No. 08/513,366, Aug. 10, 1995, abandoned, which is a continuation-in-part of application No. 08/433,108, May 3, 1995, abandoned.

[51] Int. Cl.[7] .............................. A61K 38/16; C12N 5/10; C12N 15/62; C12N 15/63
[52] U.S. Cl. ............................ 514/2; 514/12; 435/320.1; 435/69.7; 435/325; 435/252.3; 530/350; 536/23.4
[58] Field of Search .................................. 536/23.4, 23.5, 536/23.1; 530/300, 350, 324; 514/2, 12; 435/69.1, 69.3, 69.7, 252.3, 325

[56] References Cited

U.S. PATENT DOCUMENTS

| | | |
|---|---|---|
| 5,165,924 | 11/1992 | Shewen et al. . |
| 5,238,823 | 8/1993 | Potter et al. . |
| 5,273,889 | 12/1993 | Potter et al. . |
| 5,336,491 | 8/1994 | Berget et al. . |
| 5,476,657 | 12/1995 | Potter . |
| 5,506,120 | 4/1996 | Yamamoto et al. . |
| 5,557,033 | 9/1996 | Halawani . |
| 5,723,129 | 3/1998 | Potter et al. . |

FOREIGN PATENT DOCUMENTS

| | | |
|---|---|---|
| 20 14033 | 2/1993 | Canada . |
| 0 529 487 | 3/1993 | European Pat. Off. . |
| 0 591 524 | 4/1994 | European Pat. Off. . |
| WO 92/03358 | 3/1992 | WIPO . |
| WO 93/08290 | 4/1993 | WIPO . |
| WO 94/08616 | 4/1994 | WIPO . |
| WO 94/19469 | 9/1994 | WIPO . |
| WO 96/24675 | 8/1996 | WIPO . |

OTHER PUBLICATIONS

Bowie et al., "Deciphering the Message in Protein Sequences Tolerance to Amino Acid Substitutions," *Science* 247:1306–1310(1990).
Donelly et al., "Immunization with Polynucleotides: A Novel Approach to Vaccination," *The Immunologist* 2(1):20–26 (1994).
Ngo et al., "Computational Complexity, Protein Structure Prediction, and the Levinthal Paradox," The Protein Folding Problem and Tertiary Structure Prediction pp. 492–495 (1994).
Sharp et al., "The Role of Hypothalamic Vasoactive Intestinal Polypeptide in the Maintenance of Prolactin Secretion in Incubating Bantam Hens: Observations Using Passive Immunization, Radioimmunoassay and Immunohistochemistry," *J. Endocrinology* 122(1):5–13 (1989).
Wells, "Additivity of Mutational Effects in Proteins," *Biochemistry* 29(37):8509–8517 (1990).
Youngren et al., "Active Immunization with Vasoactive Intestinal Peptide Prevents the Secretion of Prolactin Induced by Electrical Stimulation of the Turkey Hypothalamus," *General and Comparative Endocrinology* 95:330–336(1994).
"DNA Cloning" vols. I and II (D.N. Glover ed.) 1985.
"Handbook of Experimental Immunology", vols. 1–10 (D.W. Weir and C.C. Blackwell eds.) *Blackwell Scientific Pub.,* (1980).
"Isolation of a Neuropeptide Corresponding to the N–Terminal 27 Residues of the Pituitary Adenylate Cyclase Activating Polypeptide with 38 Residues (PACAP38)", *Biochem. And Biophysical Research Comm.* 2:643–648(1990).
Abe et al., *Endocrinology* 116:1383–1390(1985).
Arnadout et al., *Endocrinology* 119:2052–2057(1986).
Bacon et al., *Poultry Science* 62:2400–2473(1983).
Christophe, *Biochimica et Biophysica Acta* 183–199(1993).
Donnelly et al., *The Immunologist* 2/1:20–26(1994).
El Halawani et al., *Poultry Science Suppl.* 74(6):157 Abstract #467 (1995).
El Halawani et al., *Biology of Reproduction* 52:179–183(1995).
El Halawani et al., *Poultry Science* 72:906–911(1993).
El Halawani et al., *General and Comparative Endocrinology* 80:138–145(1990).
El Halawani et al., *General and Comparative Endocrinology* 87:436–442(1992).
El Halawani et al., *General and Comparative Endocrinology* 78:66–73(1990).
El Halawani et al., *Poultry Science* 62:48(1989).
El Halawani et al., *Poultry Science* 70:38(1991).
El Halawani et al., *Poultry Science* 68:48–49(1989).
Grider et al., *Annals NY Acad. Science* 527:369–377(1988).
Hall et al., *General and Comparative Endocrinology* 62:171–184(1986).

(List continued on next page.)

*Primary Examiner*—Elizabeth Kemmerer
*Attorney, Agent, or Firm*—Robins & Associates

[57] ABSTRACT

This invention relates to vasoactive intestinal peptide ("VIP") and cross-reactive peptides. In particular, this invention relates to peptides capable of inducing antibodies which neutralize the activity of VIP. This invention also relates to tandemly repeated peptides derived from VIP or from cross-reactive peptides, which can elicit a broad immune response. The present invention is useful for increasing egg production in bird species and for increasing efficiency of feed utilization and rate of gain in food producing animals.

18 Claims, 14 Drawing Sheets

OTHER PUBLICATIONS

Haller et al., *Poultry Science* 40:155–163(1961).
Johnson, *Poultry Science* 62:2474–2478(1983).
Lea et al., *Hormones and Behavior* 25:283–294(1991).
Macnamee et al., *General and Comparative Endocrinology* 62:470–478(1990).
Maniatis et al., *Molecular Cloning: A Laboratory Manual* (1982).
March et al., *Journal of Reproduction and Fatality* 101: 227–233(1994).
Mauro et al., *Endocrinology* 125:1795–1804(1989).
Mauro et al., *Poultry Science* 70:79(1991).
Michalkiewicz et al., *Am. J. Physiol. (Endocrino. Metab. 29)* 266:E905–913(1994).
Nagy et al., *Endocrinology* 122:364–366(1988).
Nestor et al., *Poultry Science* 65:1405–1409(1986).
Nestor et al., *Poultry Science* 65:1410–1412(1986).
Opel et al., Proceedings of the Society for Experimental Biology and Medicine 187:455–460 (1988).
Pitts et al., *Poultry Science* 71: Abstract #61 (1992).
Pitts et al., *Poultry Science* 59: Abstract #177 (1993).
Proudman et al., *Poultry Science* 69:1209–1214(1990).
Proudman J.A., *Poultry Science* (Suppl. 156)74: Abstract #468(1995).
Proudman et al., Proceedings of the Society for Experimental Biology and Medicine 187:448–454(1988).
Robinson et al., *Poultry Science* 72:912–922(1993).
Rozenboim et al., *Poultry Science* 72:94 abstract #282(1993).
Rozenboim et al., *Biology of Reproduction* 48:1129–1134(1993).
Rozeboim et al., *Biology of Reproduction* 48:1246–1250(1993).
Rozeboim et al., *Biology of Reproduction* 49:622–626(1993).
Rozeboim et al., *Poultry Science* 71:21 Abstract #63 (1992).
Sharp, P.J., *Poultry Science* 72:897–905(1993).
Skwarlo–Sonta, K., *Immunology Letters* 33:105–122(1992).
Sun et al., *Poultry Science* (Suppl. 157)74: Abstract #470(1995).
Talbot et al., *Endocrinology* 129:496–502(1991).
Ulmer et al., *Curr. Opin. Invest. Drugs* 2:938–989(1993).
Wong et al., *General and Comparative Endocrinology* 62:171–184(1986).
Wong et al., *General and Comparative Endocrinology* 83:18–26(1991).
Xu et al., *Poultry Sci.* 71:21 Abstract #63(1992).
Youngren et al., *Poultry Science* (Suppl. 157)74: Abstract #4(1995).
Youngren et al., *Poultry Science* 72:133 Abstract #398(1993).
Youngren et al., *General and Comparative Endocrinology* 89:220–289(1993).
Benjamini et al. Immunology: A Short Course, Wiley–Liss, New York, p. 40, 1991.

FIGURE 1

VIP PEPTIDES

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| Chicken | H | S | D | A | V | F | T | D | N | Y | S | R | F | R | K | Q | M | A | V | K | K | Y | L | N | S | V | L | T |
| Gila Monster | H | S | D | A | I | F | T | Q | Q | Y | S | K | L | L | A | K | L | A | L | Q | K | Y | L | A | S | I | L | G |
| Sheep | H | S | D | A | V | F | T | D | N | Y | T | R | L | L | R | K | M | A | V | K | K | Y | L | N | S | I | L | N |
| Macaque | H | S | D | A | V | F | T | D | N | Y | T | R | L | R | K | Q | M | A | V | K | K | Y | L | N | S | I | L | I |
| Rabbit | H | S | D | A | V | F | T | D | N | Y | T | R | L | R | K | Q | M | A | V | K | K | Y | L | N | S | I | L | N |
| Dog | H | S | D | A | V | F | T | D | N | Y | T | R | L | R | K | Q | M | A | V | K | K | Y | L | N | S | I | L | N |
| Catshark Dogfish | H | S | D | A | V | F | T | D | N | Y | S | R | L | R | K | Q | M | A | V | K | K | Y | I | N | S | L | L | A |
| Cod | H | S | D | A | V | F | T | D | S | Y | S | R | F | R | K | Q | M | A | V | K | K | Y | L | N | S | S | L | |
| Opossum | H | S | D | A | V | F | T | D | N | Y | T | R | L | R | K | Q | M | A | A | K | K | Y | L | D | S | I | L | N |
| Mouse | H | S | D | A | V | F | T | D | N | Y | T | R | L | R | K | Q | M | A | M | K | K | Y | L | N | S | I | L | N |
| Human | H | S | D | A | V | F | T | D | N | Y | T | R | L | R | K | Q | M | A | V | K | K | Y | L | N | S | I | L | N |
| Pig | H | S | D | A | V | F | T | D | N | Y | T | R | L | R | K | Q | M | A | V | K | K | Y | L | N | S | I | L | N |
| Goat | H | S | D | A | V | F | T | D | N | Y | T | R | L | R | K | Q | M | A | V | K | K | Y | L | N | S | I | L | N |
| Guinea Pig | H | S | D | A | L | F | T | D | T | Y | T | R | L | R | K | Q | M | A | M | K | K | Y | L | N | S | V | L | N |

FIGURE 2

```
1                           28
HSDAVFTDNYTRLRKQMAVKKYLNSILN

HSDAVFTDNY      10mer
1       10

TDNYTRLRKQ      10mer
    7       16

LRKQMAVKKY      10mer
        13       22

VKKYLNSILN      10mer
            19       28
```

Figure 4a

Name: VIPo1a 150 BPS DNA
DESCRIPTION: oligo w/4 copies of VIP 1-12 with pseudo BamH1

* S E Q U E N C E *

```
  1  GATCTCATAG CGATGCGGTG TTTACCGATA ACTATACCCG TCATAGCGAT GCGGTGTTTA
 61  CCGATAACTA TACCCGTCAT AGCGATGCGG TGTTTACCGA TAACTATACC CGTCATAGCG
121  ATGCGGTGTT TACCGATAAC TATACCCGTG
```

Figure 4b

NAME: VIPo1b 150 BPS DNA
DESCRIPTION: antisense of VIP aa 1-12 w/BamH1 sites

* S E Q U E N C E *

```
  1  GATCCACGGG TATAGTTATC GGTAAACACC GCATCGCTAT GACGGGTATA GTTATCGGTA
 61  AACACCGCAT CGCTATGACG GGTATAGTTA TCGGTAAACA CCGCATCGCT ATGACGGGTA
121  TAGTTATCGG TAAACACCGC ATCGCTATGA
```

Figure 4c

NAME: VIPo2a  150 BPS DNA
DESCRIPTION: VIP aa 6-17

\* \* \* S E Q U E N C E \* \* \*

```
  1 GATCTTTTAC CGATAAACTAT ACCCGTCTGC GTAAACAGAT GTTTACCGAT AACTATACCC
 61 GTCTGCGTAA ACAGATGTTT ACCGATAACT ATACCCGTCT GCGTAAACAG ATGTTTACCG
121 ATAACTATAC CCGTCTGCGT AAACAGATGG
```

Figure 4d

NAME: VIPo2b  150 BPS DNA
DESCRIPTION: reverse complement of VIPo2a, aa 6-17

\* \* \* S E Q U E N C E \* \* \*

```
  1 GATCCCATCT GTTTACGCAG ACGGGTATAG TTATCGGTAA ACATCTGTTT ACGCAGACGG
 61 GTATAGTTAT CGGTAAACAT CTGTTTACGC AGACGGGTAT AGTTATCGGT AAACATCTGT
121 TTACGCAGAC GGGTATAGTT ATCGGTAAAA
```

Figure 4e

NAME: VIPo3a  162 BPS DNA
DESCRIPTION: vip 3 oligo

NAME: VIPo4a
DESCRIPTION: VIP aa seq 17-28, 150 BPS DN

Figure 4i

NAME: PACAPo1a    174 BPS DNA
DESCRIPTION: Sense strand of PACAP as aa 11-24 with 3 PACAP aa

\*\*\* S E Q U E N C E \*\*\*

```
  1 GATCTAGCCG TTATCGTAAA CAGATGGCGG TGAAAAAATA TCTGGCGAGC CGTTATCGTA
 61 AACAGATGGC GGTGAAAAAA TATCTGGCGA GCCGTTATCG TAAACAGATG GCGGTGAAAA
121 AATATCTGGC GAGCCGTTAT CGTAAACAGA TGGCGGTGAA AAAATATCTG GCGG
```

Figure 4j

NAME: PACAPo1b    174 BPS DNA
DESCRIPTION: Antisense of PACAPo1a

\*\*\* S E Q U E N C E \*\*\*

```
  1 GATCCCGCCA GATATTTTTT CACCGCCATC TGTTTACGAT AACGGCTCGC CAGATATTTT
 61 TTCACCGCCA TCTGTTTACG ATAACGGCTC GCCAGATATT TTTCACCGC CATCTGTTTA
121 CGATAACGGC TCGCCAGATA TTTTTTCACC GCCATCTGTT TACGATAACG GCTA
```

Figure 4k

NAME: PACAPo1a  90 BPS DNA
DESCRIPTION: Sense strand of PACAP as aa 11-24 with 3 PACAP aa

* SEQUENCE *

```
 1 GATCTAGCCG TTATCGTAAA CAGATGGCGG TGAAAAAATA TCTGGCGAGC CGTTATCGTA
61 AACAGATGGC GGTGAAAAAA TATCTGGCGG
```

Figure 4l

NAME: PACAPo1b  90 BPS DNA
DESCRIPTION: Antisense of PACAPo1a

* SEQUENCE *

```
 1 GATCCCGCCA GATATTTTTT CACCGCCATC TGTTTACGAT AACGGCTCGC CAGATATTTT
61 TTCACCGCCA TCTGTTTACG ATAACGGCTA
```

Figure 4m

NAME: VIPo2a  78 BPS DNA
DESCRIPTION: VIP aa 6-17

NAME: VIPo3a
DESCRIPTION: VIP 3 oligo     84 BPS DNA

* SEQUENCE *

1   GATCTACCCG TCTGCGTAAA CAGATGGCGG TGAAAAAATA TCTGACCCGT CTGCGTAAAC
61  AGATGGCGGT GAAAAAATAT CTGG

Figure 4p

NAME: VIPo3b
DESCRIPTION: reverse complement of VIP o3a     84 BPS DNA

* SEQUENCE *

1   GATCCCAGAT ATTTTTTCAC CGCCATCTGT TTACGCAGAC GGGTCAGATA TTTTTTCACC
61  GCCATCTGTT TACGCAGACG GGTA

Figure 4q

NAME: VIPo4a 78 BPS DNA
DESCRIPTION: VIP aa seq 17-23, E.coli bias, 4 copy

* S E Q U E N C E *

```
 1  GATCTATGGC GGTGAAAAAA TATCTGAACA GCATTCTGAA CATGGCGGTG AAAAAATATC
61  TGAACAGCAT TCTGAACG
```

Figure 4r

NAME: VIPo4b 78 BPS DNA
DESCRIPTION: reverse complement of VIPo4a, aa 17-23

* S E Q U E N C E *

```
 1  GATCCGTTCA GAATGCTGTT CAGATATTTT TTCACCGCCA TGTTCAGAAT GCTGTTCAGA
61  TATTTTTTCA CCGCCATA
```

Figure 4s

NAME: VIPo1a 78 BPS DNA
DESCRIPTION: oligo w/2 VIP aa 1-12 with pseudo BamH1

* * * S E Q U E N C E * * *

```
 1  GATCTCATAG CGATGCGGTG TTTACCGATA ACTATACCCG TCATAGCGAT GCGGTGTTTA
61  CCGATAACTA TACCCGTG
```

Figure 4t

NAME: VIPo1b 73 BPS DNA
DESCRIPTION: antisense of VIP aa 1-12 w/BamH1 sites

* * * S E Q U E N C E * * *

```
 1  GATCCACGGG TATAGTTATC GGTAAACACC GCATCGCTAT GACGGGTATA GTTATCGGTA
61  AACACCGCAT CGCTATGA
```

FUSION PROTEINS COMPRISING VASOACTIVE INTESTINAL PEPTIDE OR PACAP

This application is related to International Application No. PCT/CA96/00280 May 3, 1996, from which priority is claimed pursuant to 35 U.S.C. §371 and which application is incorporated herein by reference in its entirety, which is a continuation-in-part of U.S. patent application Ser. No. 08/513,366, filed Aug. 10, 1995, now abandoned, which is a continuation-in-part of U.S. patent application Ser. No. 08/433,108, filed May 3, 1995, now abandoned, from which applications priority is claimed pursuant to 35 U.S.C. §120, and which applications are incorporated herein by reference in their entireties.

This invention relates to vasoactive intestinal peptide ("VIP") and cross-reactive peptides. In particular, this invention relates to peptides capable of inducing antibodies which neutralize the activity of VIP. This invention also relates to tandemly repeated peptides derived from VIP or from cross-reactive peptides, which can elicit a broad immune response. The present invention is useful for increasing egg production in bird species and for increasing efficiency of feed utilization and rate of gain in food producing animals.

BACKGROUND OF THE INVENTION

VIP has been proven to be a potent releaser of avian prolactin ("PRL") in vivo and in vitro. Prolactin is a hormone produced by the anterior pituitary and it is well established that prolactin can initiate incubation behaviour in birds such as turkeys, bantam hens and many species of wild birds.

Incubation behaviour leads to early cessation of egg laying and has a fundamental role in avian reproduction. The incubation behaviour has been of great interest to scientists and producers of hatching eggs and of particular interest in the field of turkey breeding since reproductive efficiency of turkey hens is low in comparison with chickens. This low efficiency has been associated with incubation behaviour and there is convincing evidence that increased PRL secretion causes reduction in circulating gonadotropins, ovarian regression, and the shift from the egg laying to the incubation phase of the reproductive cycle in the turkey.

Incubation behaviour may be suppressed by blocking the biological effect of VIP on prolactin induction. Passive immunization of incubating chickens with anti-VIP serum has been found to induce a reduction in plasma PRL and pituitary PRL mRNA, resulting in termination of incubation behaviour. Active immunization of female turkeys with chicken VIP has also been reported to suppress circulating PRL and inhibit the expression of incubation behaviour resulting in a substantial increase in egg production. Therefore, active and passive immunization against VIP may be useful for modifying the egg-laying performance of avian species. Among the desired effects are that hens lay eggs for a longer period of time, that there is an increase in the number of eggs laid, and that non-laying hens commence laying eggs.

Further, VIP was initially identified for its vasoactive properties in mammals. VIP causes relaxation of isolated gastric and intestinal smooth muscle cells. VIP-induced relaxation is mediated by high-affinity VIP receptors and can be inhibited by VIP antiserum and selective VIP antagonists. Critical affected segments of the gastrointestinal tract occur at the pyloric-duodenal junction, the junction between the small intestine and the large intestine, and the anal sphincter. Immunization of food-producing animals against VIP may result in increased tone of these segments leading to increased efficacy of absorption of food with a consequent increased rate of feed efficiency and rate of weight gain.

Immunization against VIP presently entails chemically synthesizing the full length of VIP and conjugating the resulting peptide to a carrier molecule. Commercial application of this non-recombinant technique is expensive and difficult, and moreover conjugation of the VIP with a carrier molecule is highly unpredictable, therefore resulting in low yields of useful antigenic proteins. Further, this technique would require, firstly, a ready source of VIP antigens and, further, antigens which can elicit a broad immune response. These immunogens are not currently available. Thus, it is desirable to develop a recombinant system whereby antigenic fusion proteins are made and the conjugation step is avoided.

SUMMARY OF THE INVENTION

Accordingly, the present invention relates to a nucleotide sequence comprising (1) a DNA sequence coding for at least one copy of vasoactive intestinal peptide, and/or at least one copy of a cross-reactive protein, and/or at least one copy of a peptide fragment derived from vasoactive intestinal peptide and/or a cross-reactive peptide, and optionally (2) a DNA sequence coding for a carrier molecule, said nucleotide sequence encoding a recombinant protein capable of producing antibodies which neutralize vasoactive intestinal peptide in vivo.

Another aspect of the present invention relates to the above nucleotide sequence wherein the at least one copy of vasoactive intestinal peptide and/or cross-reactive protein and/or peptide fragment derived from vasoactive intestinal peptide and/or cross-reactive peptide is tandemly repeated. The tandemly repeated sequences may be the whole nucleotide sequence for VIP or a cross-reactive protein, or fragments of nucleotide sequences for VIP or a cross-reactive protein. Further the nucleotide sequence containing these tandemly repeated nucleotide sequences may be homopolymeric or heteropolymeric. For example, a homopolymeric nucleotide sequence may include tandem repeats of identical whole nucleotide sequences or identical fragments of nucleotide sequences for VIP or a cross-reactive protein. A heteropolymeric nucleotide sequence may include whole nucleotide sequences from different species, or different nucleotide sequences taken from the same or different species.

Yet another aspect of the present invention is a recombinant protein comprising (1) at least one peptide derived from (a) vasoactive intestinal peptide and/or (b) a cross-reactive protein and/or © a fragment derived from vasoactive intestinal peptide and/or a cross-reactive protein, and optionally (2) a carrier molecule, said recombinant protein being capable of producing antibodies which neutralize vasoactive intestinal peptide in vivo. Preferably the recombinant protein is a fusion protein of the at least one peptide and the carrier molecule.

The recombinant protein may also be a fusion protein of tandem repeats of the peptide derived from VIP or the cross-reactive protein or fragments thereof. The tandemly repeated segment may be one or more identical or different whole VIP's or cross-reactive proteins, or fragments thereof. Further, the recombinant protein containing these tandemly repeated sequences may be homopolymeric or heteropolymeric. For example, a homopolymeric protein may include tandem repeats of identical whole sequences or identical fragments of VIP or a cross-reactive protein. A heteropolymeric protein may include whole sequences of VIP or a cross-reactive protein from different species, or different fragments thereof taken from the same or different species.

The recombinant proteins of the present invention are useful in the active and passive immunization against VIP of egg-laying birds and of food-producing animals.

This invention also relates to methods of actively or passively immunizing an egg-laying bird or food-producing animal against VIP comprising treating the bird or animal with the above-mentioned fusion protein or nucleotide sequence.

BRIEF DESCRIPTION OF THE FIGURES

FIG. 1 is a table depicting the amino acid sequence of VIP from various animal species in which:

- SEQ ID NO:1 is the amino acid sequence for Chicken VIP,
- SEQ ID NO:2 is the amino acid sequence for Gila Monster VIP,
- SEQ ID NO:3 is the amino acid sequence for Sheep VIP,
- SEQ ID NO:4 is the amino acid sequence for Macaque VIP,
- SEQ ID NO:5 is the amino acid sequence for Rabbit VIP,
- SEQ ID NO:6 is the amino acid sequence for Dog VIP,
- SEQ ID NO:7 is the amino acid sequence for Catshark Dogfish VIP,
- SEQ ID NO:8 is the amino acid sequence for Cod VIP,
- SEQ ID NO:9 is the amino acid sequence for Opossum VIP,
- SEQ ID NO:10 is the amino acid sequence for Mouse VIP,
- SEQ ID NO:11 is the amino acid sequence for Human VIP,
- SEQ ID NO:12 is the amino acid sequence for Pig VIP,
- SEQ ID NO:13 is the amino acid sequence for Goat VIP,
- SEQ ID NO:14 is the amino acid sequence for Guinea Pig VIP;

FIG. 2 depicts the amino acid sequences for each of four nested peptides derived from VIP in which:

- SEQ ID NO:3 is the amino acid sequence for Sheep VIP (representing the consensus amino acid sequence for VIP),
- SEQ ID NO:15 is the amino acid sequence of the peptide corresponding to VIP's amino acids 1–10,
- SEQ ID NO:16 is the amino acid sequence of the peptide corresponding to VIP's amino acids 7–16,
- SEQ ID NO:17 is the amino acid sequence of the peptide corresponding to VIP's amino acids 13–22,
- SEQ ID NO:18 is the amino acid sequence of the peptide corresponding to VIP's amino acids 19–28;

FIG. 3 depicts various plasmid DNA constructs, the nucleotide bases of which code for nested peptides derived from VIP and for a cross-reactive peptide derived from pituitary adenylate cyclase activating protein (PACAP) in which:

- SEQ ID NO:3 is the amino acid sequence for Sheep VIP (representing the consensus amino acid sequence for VIP),
- SEQ ID NO:13 is the amino acid sequence of V1, the VIP-derived peptide corresponding to VIP's amino acids 1–12,
- SEQ ID NO:20 is the amino acid sequence of V2, the VIP-derived peptide corresponding to VIP's amino acids 6–17,
- SEQ ID NO:21 is the amino acid sequence of V3, the VIP-derived peptide corresponding to VIP's amino acids 11–23,
- SEQ ID NO:22 is the amino acid sequence of V4, the VIP-derived peptide corresponding to VIP's amino acids 17–28,
- SEQ ID NO:23 is the amino acid sequence of P1, the PACAP-derived peptide corresponding to VIP's amino acids 14–23 plus four additional PACAP-specific amino acids (the first three and the last one);

FIG. 4, comprising FIGS. 4*a* to 4*t*, depicts the sequences of the oligonucleotides that encode tandem repeats of the four peptides derived from VIP (V1, V2, V3 and V4) and PACAP (P1) exemplified in FIG. 3 and SEQ ID NO:3 and 19–23 in which:

- FIG. 4*a* (SEQ ID NO:24) encodes a 150 base pair DNA sequence coding for V1 (SEQ ID NO:19),
- FIG. 4*b* (SEQ ID NO:25) encodes a 150 base pair DNA sequence coding for antisense of V1,
- FIG. 4*c* (SEQ ID NO:26) encodes a 150 base pair DNA sequence coding for V2 (SEQ ID NO:20),
- FIG. 4*d* (SEQ ID NO:27) encodes a 150 base pair DNA sequence coding for antisense of V2,
- FIG. 4*e* (SEQ ID NO:28) encodes a 162 base pair DNA sequence coding for V3 (SEQ ID NO:21),
- FIG. 4*f* (SEQ ID NO:29) encodes a 162 base pair DNA sequence coding for antisense of V3,
- FIG. 4*g* (SEQ ID NO:30) encodes a 150 base pair DNA sequence coding for V4 (SEQ ID NO:22),
- FIG. 4*h* (SEQ ID NO:31) encodes a 150 base pair DNA sequence coding for antisense of V4,
- FIG. 4*i* (SEQ ID NO:32) encodes a 174 base pair DNA sequence coding for the amino acid sequence of P1 (SEQ ID NO:23),
- 1 FIG. 4*j* (SEQ ID NO:33) encodes a 174 base pair DNA sequence coding for antisense of P1,
- FIG. 4*k* (SEQ ID NO:34) encodes a 90 base pair DNA sequence coding for a portion of the amino acid sequence of P1 (SEQ ID NO:23),
- FIG. 4*l* (SEQ ID NO:35) encodes a 90 base pair DNA sequence coding for antisense of a portion of P1,
- FIG. 4*m* (SEQ ID NO:36) encodes a 78 base pair DNA sequence coding for a portion of V2 (SEQ ID NO:20),
- FIG. 4*n* (SEQ ID NO:37) encodes a 78 base pair DNA sequence coding for antisense of a portion of V2,
- FIG. 4*o* (SEQ ID NO:38) encodes a 84 base pair DNA sequence coding for a portion of V3 (SEQ ID NO:21),
- FIG. 4*p* (SEQ ID NO:39) encodes a 84 base pair DNA sequence coding for antisense of a portion of V3,
- FIG. 4*q* (SEQ ID NO:40) encodes a 78 base pair DNA sequence coding for a portion of V4 (SEQ ID NO:22),
- FIG. 4*r* (SEQ ID NO:41) encodes a 78 base pair DNA sequence coding for antisense of a portion of V4,
- FIG. 4*s* (SEQ ID NO:42) encodes a 78 base pair DNA sequence coding for a portion of V1 (SEQ ID NO:19),
- FIG. 4*t* (SEQ ID NO:43) encodes a 78 base pair DNA sequence coding for antisense of a portion of V1; and FIG. 5 depicts the immunoreactivity of a fusion protein comprising (1) VIP and SEQ ID NO:3 or a peptide derived from VIP, namely V2 (SEQ ID NO:20) and (2) a carrier molecule, namely leukotoxin, in which bacterial lysates were prepared and subjected to SDS-PAGE and Western blotting as described herein.

DISCLOSURE OF THE INVENTION

Nested peptides are derived from the 28 amino acid VIP molecule secreted by various animal species, including, for example, any of the ones listed in FIG. 1 and SEQ ID NOS:1–14. For example, three to six nested peptides are prepared, each being 6 to 12 (and preferably 8 to 10) amino acids in length. The nested peptides are then tested to identify those which are capable of raising antibodies which will neutralize VIP in vivo.

At least the following two approaches can be used to identify the desired segments. Oligonucleotides corresponding to each of the nested peptides are synthesized and cloned into a carrier protein gene such as leukotoxin ("Lkt") and the resulting protein encoded by the chimeric gene is tested for its ability to react with antibodies which neutralize the biological effect of VIP in vivo. Alternatively, each of the individual short peptides are chemically synthesized and then chemically conjugated to a carrier molecule such as ovalbumin. These conjugates are individually tested for their ability to react with antibodies which neutralize the biological effect of VIP in vivo.

One or more of the nested peptides having the desired effect is identified and its nucleotide sequence inserted into the DNA coding for a carrier protein such as Lkt. One copy of the nucleotide sequence may be inserted. Alternatively, tandem repeats of one or more such sequences may be inserted resulting in a multimer.

Proteins homologous to VIP, such as pituitary adenylate cyclase activating protein ("PACAP"), can be used to accomplish the same objectives in any manner equivalent to that with respect to a peptide derived from VIP. PACAP appears to outcompete VIP for its own receptor and therefore may be a better anti-VIP antigen than VIP itself. PACAP may also have an added advantage in that its presence correlates with innappetance and accordingly it appears to be involved in the control of feeding behaviour.

Other molecules exhibiting structural homology with VIP should also be useful with respect to the present invention. These include proteins such as PH1, PHV(1-42) helodermin and others, summarized in Table 1 of a review article by Jean Christophe in *Biochimica et Biophysica Acta* (1993) 1154:183–199.

The carrier protein serves the function of rendering the fusion product more immunogenic. A carrier protein may not be essential where the tandemly repeated sequences of VIP or fragments thereof form the fusion product. Lkt is but one possible carrier protein, and others can be selected. Preferably, the carrier protein has a molecular weight in the range of 25 to 100 kDa.

The carrier protein, such as Lkt, may be placed into a replicable expression vector before or after the insertion of the VIP or related nucleotide sequence(s). The vector is used to transform a suitable host cell and the transformed host cell is cultured to effect the production of the recombinant fusion protein. The recombinant protein thereby provides a ready source of VIP immunogen useful for producing antibodies which neutralize VIP in vivo without inducing prolactin release.

An aspect of the present invention is to provide a VIP immunogen capable of eliciting a broad immune response. The present invention therefore includes a gene construct comprising (preferably different) full length sequences in tandem that may be connected to a carrier protein gene such as the Lkt gene. The VIP gene sequences may be from macaque, gila monster and opossum or any other combination of VIP or cross-reactive protein gene sequences from different species with variances in the amino acid sequence of VIP.

The desired gene construct can be made by tandemly ligating VIP cDNA sequences from different species to a DNA coding for a carrier protein. The resulting DNA construct is placed into an expression vector and the vector used to transform a suitable host. The resulting recombinant protein is useful in eliciting a broad immune response in different target species.

The invention also relates to a nucleotide sequence which encodes a protein as described variously above, which nucleotide sequence is directly capable of functioning as a vaccine to neutralize the effect of VIP in vivo. Generally, injection of DNA encoding a foreign protein into skeletal or cardiac muscle results in the muscle cells taking up the exogenous DNA. This causes transfection of the muscle cells with the DNA resulting in expression of the foreign protein by the muscle cells. This, in turn, results in both antibodies and cytotoxic T lymphocytes being elicited, allowing for immunization against the foreign protein. See Donnelly, J. J., Ulmer, J. E., and Liu, M. A. "Immunization with Polynucleotides: A Novel Approach to Vaccination", *The Immunologist* (1994) 2/1:20–26.

DETAILED DESCRIPTION OF THE PREFERRED EMBODIMENT

The practice of the present invention employs conventional techniques of molecular biology, microbiology, recombinant DNA technology and immunology which are within the skill of the art. Such techniques are explained fully in the literature. See, for example Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984) and *Handbook of Experimental Immunology*, Vols. I–IV (D. M. Weir and C. C. Blackwell eds., 1986, Blackwell Scientific Publications).

Figure 3:
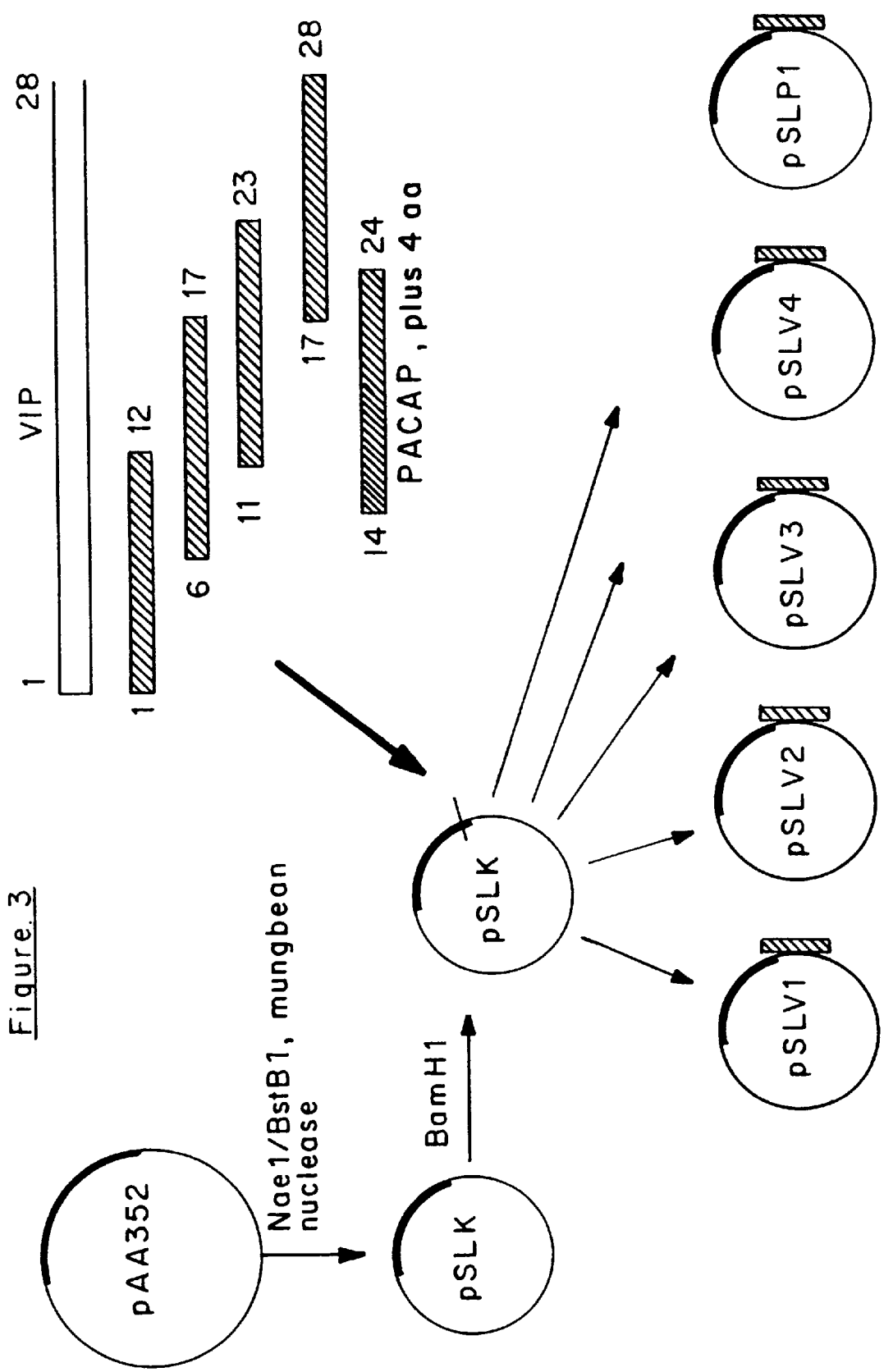

Vector and carrier protein gene construct: The *Pasteurella hemolytica* Lkt molecule serves as the carrier protein. Plasmid pAA352 (Canadian Patent No. 2,014,033) U.S. Pat. No. 5,476,657 serves as the starting point or root vector. It consists of the Lkt gene (approximately 2800 base pairs) in the vector pGH433laci (approximately 4595 base pairs) where the gene is bound by a 5' Bglii vector site and a 3' BamH1 vector site. The Lkt gene has been shortened to 1470 base pairs by the excision of the internal BstB1/Nae1 fragment and its open reading frame maintained by mungbean exonuclease digestion and religation. The resulting plasmid has been designated pSLK (see FIG. 3). This version of the Lkt gene, when expressed in *E. coli*, results in the production of a 52 kDA protein.

Figure 4E:
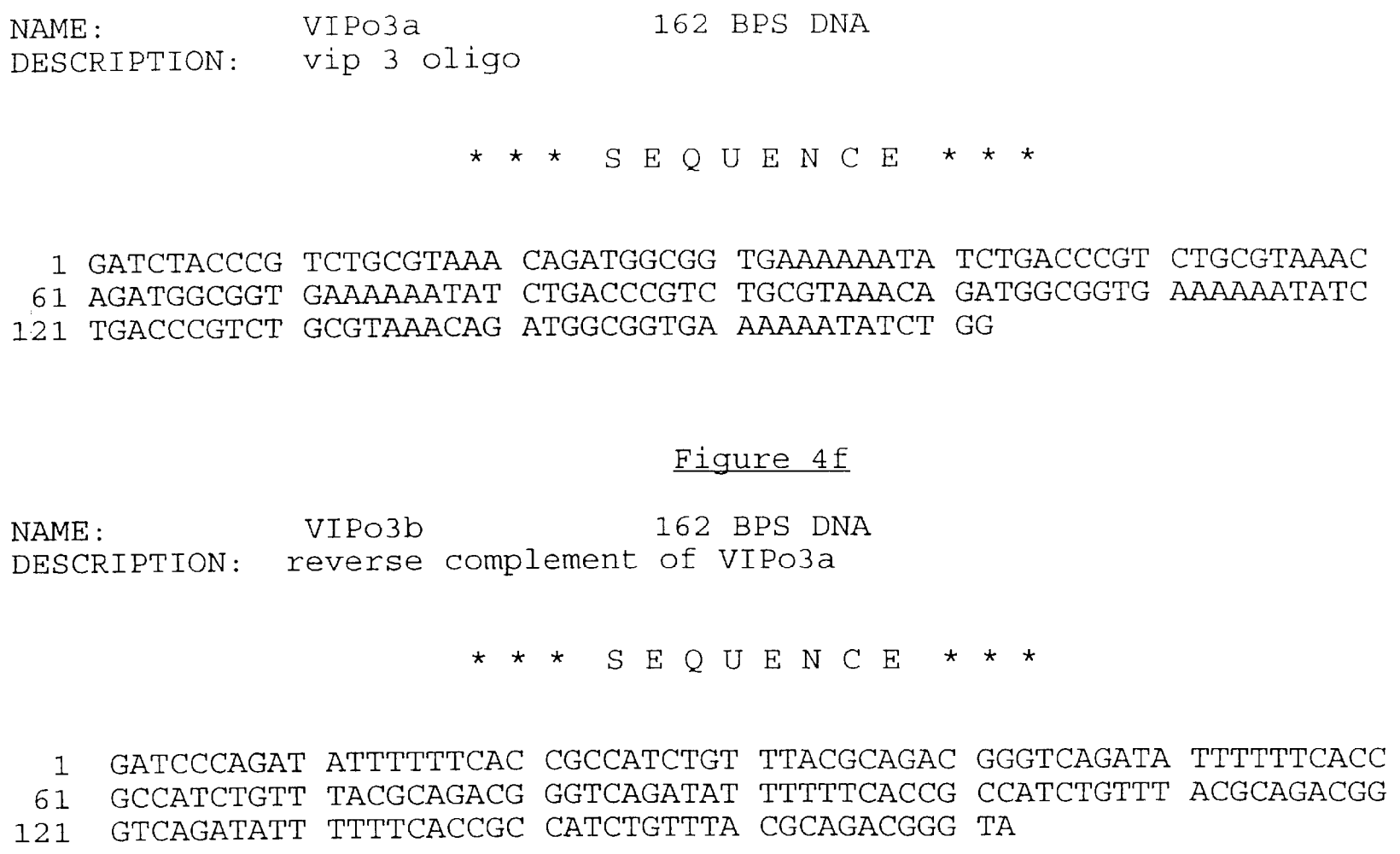
Figure 4G:
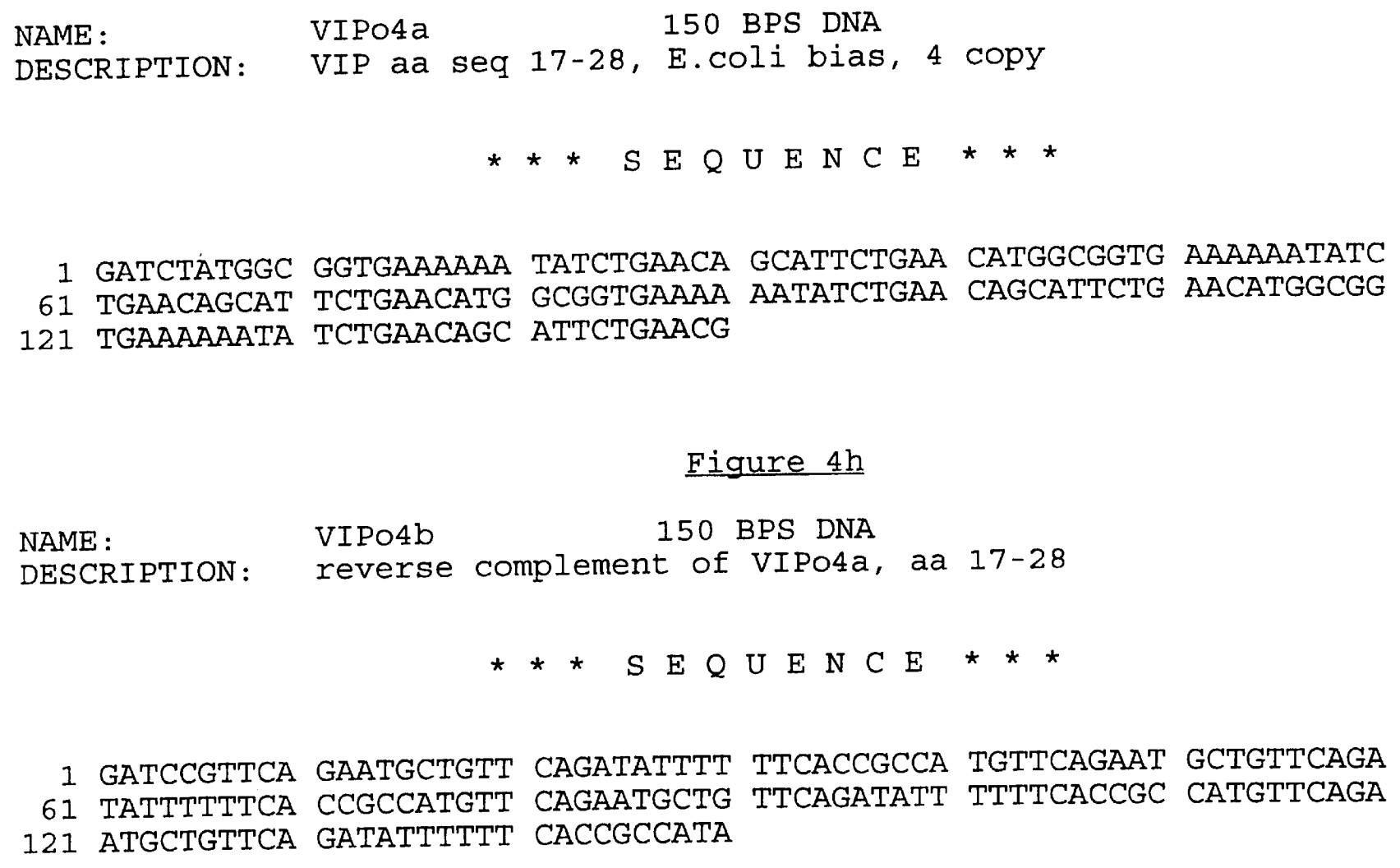

VIP and PACAP peptides and oligonucleotides: VIP is found as a 28 amino acid protein in most mammalian species (see FIG. 1 and SEQ ID NOS:1–14). To determine which peptide derivatives of this molecule best function as blocking or neutralizing B-cell epitopes, the following gene constructs are synthetically prepared from the consensus sequence (HSDAVFTDNYTRLRKQMAVKKYLNSILN, see SEQ ID NO:3): V1, amino acids 1–12 and SEQ ID NO:19; V2, amino acids 6–17 and SEQ ID NO:20; V3, amino acids 11–23 and SEQ ID NO:21; and V4, amino acids 17–28 and SEQ ID NO:22, where each of these is synthesized at the nucleotide level in four contiguous copies. In addition, a PACAP construct, P1 and SEQ ID NO:23, is prepared based on the region of homology with VIP. This sequence corresponds to amino acids 14–23 of VIP and also has four additional PACAP-specific amino acids (in bold and underlined) SRYRKQMAVKKYLA (SEQ ID NO:23): The oligonucleotides that encode each of these five peptide-oligomers have been designed such that only the 3' end cloning site is regenerated after subcloning into pSLK at the end of the Lkt gene. The nucleotide sequence of each of these peptide repeats is set out in FIGS. 4a to 4t and SEQ ID NOS:24–43. These oligomers are initially expressed as fusion proteins at the carboxy-terminal end of the Lkt in pSLK. The five resulting constructs have been identified as pSLV1, pSLV2, pSLV3, pSLV4 and pSLP1 (see FIG. 3). These constructs encode for, respectively, multimers of the four peptides derived from VIP, namely V1, V2, V3 and V4 (SEQ ID NOS:19–22, respectively), and the peptide derived from PACAP, namely P1 (SEQ ID NO:23).

Once their antigenicity is confirmed, the constructs are used to develop the appropriate animal model, using standard immunological testing methods, in other words, a model that is based on the ability to elicit VIP-neutralizing antibody. Using similar techniques, other constructs can be prepared from non-consensus VIP sequences and from potentially variable different nested sequences, as well as from cross-reactive peptides. Useful constructs are selected based on immunogenicity (biologically relevant antigenicity), B-cell epitope molarity, and expression levels, etc.

Protein Production: These above-mentioned constructs are expressed as inclusion bodies in *E. coli* as follows: 10 ml of LB-broth containing 100 μg/ml of ampicillin can be inoculated with 5–10 colonies of the recombinant *E. coli* and incubated at 37° C. for six hours on a G10 shaker at 220 RPM. Four ml of these cultures are diluted into each of two baffled Fernbach flasks containing 400 ml of LB broth and ampicillin and incubated overnight. Cells are then harvested by centrifugation for 10 minutes at 4,000 RPM in 500 ml polypropylene bottles, using a Sorvall GS3 rotor. Pellets are resuspended in two equal 400 ml volumes of LB broth containing ampicillin which has been prewarmed to 37° C., and the cells are then incubated for 2 hours.

Isopropyl-β,D-thiogalactopyranoside ("IPTG"), 500 mM in double deionized water, is added to a final concentration of 1 mM in order to induce the synthesis of the recombinant protein (Lkt-VIP fusions). Cultures are then incubated a further 2–4 hours. Cells are harvested by centrifugation as above and resuspended in 30 ml of 50 mM Tris-hydrochloride, 25% (w/v) sucrose, pH 8.0, and frozen at −70° C. The frozen cells are then thawed at room temperature and 5 ml of lysozyme (20 mg/ml in 250 mM Tris-HCl at pH 8.0) added. The mixture is vortexed at high speed for 10 seconds and placed on ice for 15 minutes. The cells are then added to 500 ml of lysis buffer (100 mM Tris-HCl, pH 8.0, 50 mM EDTA, 2% Trition X-100) in a 1 L beaker and mixed by stirring with a 2 ml pipette. This solution is placed on ice and sonicated for 30 second bursts five times (with 1 minute cooling time between bursts) using a Braun sonicator and a large probe set at 100 watts of power. Equal volumes of the solution are then placed in Teflon SS34 centrifuge tubes and centrifuged for 20 minutes at 10,000 RPM in a Sorvall SS34 rotor. The pellets are then resuspended in a total of 100 ml of sterile double deionized water by vortexing at high speed and then centrifuging as above. Supernatants are discarded and the pellets are combined in 20 ml of Tris Buffer Solution ("TBS") (10 mM Tris-HCl, 150 mM NaCl, pH 8.0) and frozen at −20° C.

The recombinant inclusion bodies are then solubilized by thawing at room temperature and adding 100 ml of 8 M guanidine-HCl in TBS and mixing vigorously with a magnetic stir bar at room temperature for 30 minutes. Solutions are then transferred to a 2 L flask and 1200 ml of TBS added and further mixed for 2 hours. Aliquots of 500 ml are placed in dialysis tubing (6–8,000 kDa cut off) and dialyzed against TBS+0.5 M guanidine-HCl for 12 hours. The dialysis buffer is then replaced with TBS+0.05M guanidine-HCl and dialyzed for a further 12 hours. The dialysis buffer is then replaced with TBS alone and dialyzed for 12 hours. This latter step is repeated three additional times. The final solution is made to 1 mM phenyl methyl sufonyl fluoride ("PMSF") to inhibit protease activity and stored at −20° C. in aliquots.

Immunoreactivity of the fusion proteins: These above-mentioned fusion proteins are tested for their ability to react with antibodies which neutralize the biological effect of VIP in vivo as follows: lysates of *E. coli* transformed with the above-mentioned constructs are prepared and subjected to SDS-PAGE and Western blotting as described below:

SDS-PAGE MINIGEL: The working solutions required are as follows:

(1) Terrific Broth ("TB"): 12 g of bacto-tryptone, 24 g of bacto-yeast extract, and 4 ml of glycerol are dissolved in distilled water ("$dH_2O$") to a final volume of 900 ml. The medium is autoclaved for 20 min at 15 lb/sq. in. on liquid cycle. The medium is allowed to cool and 100 ml of a 0.17 M $KH_2PO_4$ and 0.72 M $K_2HPO_4$ solution is added. (This solution is made by dissolving 2.31 g of $KH_2PO_4$, 12.54 g of $K_2HPO_4$ in a final volume of 100 ml of $dH_2O$.)

(2) 30% Acrylamide/Bis solution: 146 g of acrylamide and 4 g of N,N'-methylenebisacrylamide are dissolved in double-distilled water ("$ddH_2O$") to a final volume of 500 ml. Approximately 10 to 15 g of Amberlite MB-3 is added and the resulting solution stirred for 30 min. The solution is then filtered and stored at 4° C. in the dark.

(3) 1.5 M Tris solution: the pH is adjusted to 8.8 with HCl.

(4) 0.5 M Tris solution: the pH is adjusted to 6.8 with HCl.

(5) 10% SDS solution.

(6) 10% Ammonium persulphate (APS): 1 g of ammonium persulphate is dissolved in 9 ml of $ddH_2O$.

(7) N,N,N',N'-tetramethylethylenediamine (TEMED).

(8) Sample buffer (1×): 1 ml of 0.5 M Tris-HCl pH 6.8, 2 ml of 80% Glycerol, 1.6 ml of 10% SDS, 0.4 ml of 2-mercaptoethanol and 50 μl of 4% bromophenol blue are mixed together in 26.9 ml of $ddH_2O$.

(9) 5× Running buffer (pH 8.3): 15 g of Tris, 72 g of Glycine and 5 g of SDS are dissolved in 1 liter of $dH_2O$.

(10) Coomassie blue stain solution: 1 g of Coomassie blue is dissolved in 400 ml of methanol and 100 ml of Acetic acid, the volume is adjusted to 1 liter with $dH_2O$.

(11) Destain solution: 20% Methanol and 10% Acetic acid in $dH_2O$.

(12) Gel drying solution: 10% Glycerol is dissolved in the destain solution.

The method comprises inoculating 5 ml of Terrific Broth containing 100 μg/ml Ampicillin ("TB-amp") with a single colony of transformed *E. coli* which is then grown at 37° C. overnight with shaking. 5 ml of TB-amp is inoculated with 50 µl of the above-mentioned overnight culture from single colony and grown at 37° C. on a shaker (250 rpm) until a OD$_{600}$ 0.5–0.6 is reached. 800 µl of the culture is then transferred to a 1.5 ml centrifuge tube as an uninduced control ("uninduced control"), and 40 µl of 0.5 M IPTG is added to the test tube ("induced culture") which is incubated for an additional 2 hours. 500 µl of the induced culture is transferred to a 1.5 ml centrifuge tube. Both the 500 µl of induced culture and the 800 µl of uninduced culture are centrifuged for 3 min at 12000 rpm. The supernatants are discarded and the cells suspended in 100 µl of 1× sample buffer, and can be stored at −20° C.

The desired percentage of SDS-PAGE gel is prepared according to separation range (see Table 1 below). The resolving gel solution can be made according to Table 2 (see below). The gel (about 4–4.5 ml) is casted, then 100–200 µl of 1-Butanol (ddH$_2$O saturated) is carefully added on top of the resolving gel. The butanol is washed away with ddH$_2$O when the gel has polymerized and the excessive ddH$_2$O is removed with Whatman filter paper. The stacking gel is then casted according to Table 3 (see below) and the comb inserted.

The protein sample is heated at 95° C. for 10 min before loading on the SDS-PAGE gels. 5–10 µl of each sample is loaded into each well. The gel is then run at 170–180 volts until the blue dye front reaches the bottom of the gel. The gel is then stained for 30 min in the staining solution on a shaker. The gel is destained with the destain solution. The destain solution is changed until the background is clear. The gel is then soaked in the gel drying solution for approximately 10 to 30 min, then dried at 37° C. overnight between 2 pieces of cellophane membranes wetted with the gel drying solution.

TABLE 1

Range of molecular weight separation for different % of SDS-PAGE gels

| Percentage of the gel | Efficient range of separation |
| --- | --- |
| 7.5% | 65–130 Kd |
| 10% | 30–70 Kd |
| 12% | 20–50 Kd |
| 15% | 15–40 Kd |

TABLE 2

SDS-PAGE resolving gel

| Gel % | ddH$_2$O (ml) | 10% SDS (µl) | 1.5M Tris (pH 8.8) (ml) | Acryl/Bis 30% (ml) | 10% APS (µl) | TEMED (µl) |
| --- | --- | --- | --- | --- | --- | --- |
| 5 | 5.6 | 100 | 2.5 | 1.7 | 100 | 10 |
| 7 | 5.0 | 100 | 2.5 | 2.3 | 100 | 10 |
| 7.5 | 4.8 | 100 | 2.5 | 2.5 | 100 | 10 |
| 9 | 4.3 | 100 | 2.5 | 3.0 | 100 | 10 |
| 10 | 3.8 | 100 | 2.5 | 3.5 | 100 | 10 |
| 11 | 3.7 | 100 | 2.5 | 3.7 | 100 | 10 |
| 12 | 3.3 | 100 | 2.5 | 4.0 | 100 | 10 |
| 14 | 2.7 | 100 | 2.5 | 4.7 | 100 | 10 |
| 15 | 2.3 | 100 | 2.5 | 5.0 | 100 | 10 |

TABLE 3

SDS-PAGE stacking gel

| Gel % | ddH2O (ml) | 10% SDS (µl) | 0.5M Tris (pH 6.8) (ml) | Acryl/Bis 30% (µl) | 10% APS (µl) | TEMED (µl) |
| --- | --- | --- | --- | --- | --- | --- |
| 3 | 4.0 | 50 | 1.25 | 500 | 25 | 10 |
| 4 | 3.8 | 50 | 1.25 | 650 | 50 | 10 |

Figure 5:
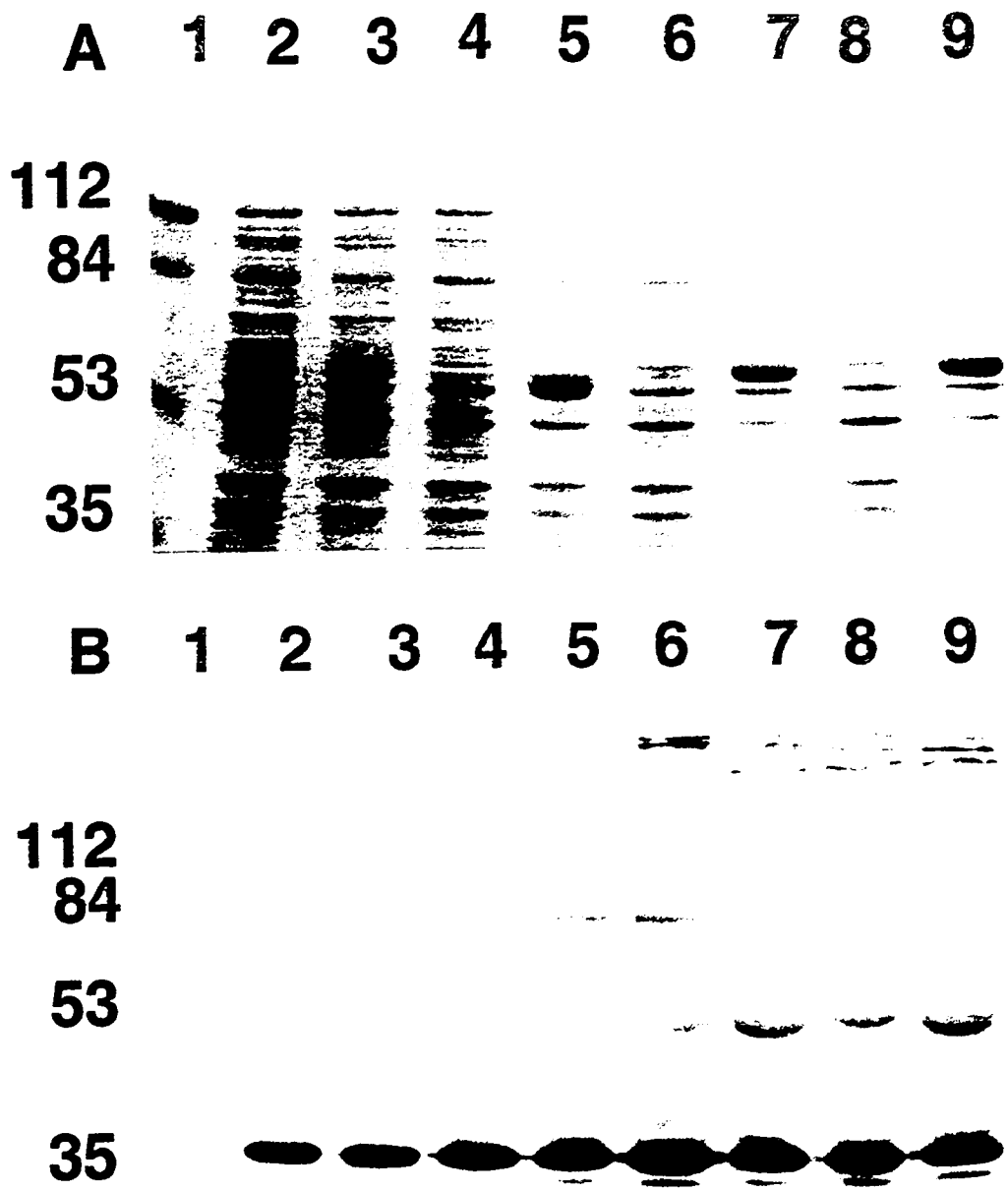

The example illustrated in FIG. 5 demonstrates the immunoreactivity of a fusion protein comprising (1) VIP (SEQ ID NO:3) or a peptide derived from VIP, namely V2 (SEQ ID NO:20), and (2) a carrier molecule, namely leukotoxin. *E. coli* were transformed with the above-mentioned constructs, lysates of the cells were prepared and subjected to SDS-PAGE as described above.

Frame A of FIG. 5 illustrates the results of the Coomassie Brilliant-Blue stained SDS-PAGE minigel. Lane 1 is the profile of molecular weight markers (112, 84, 53, and 35 kDa). Lanes 2, 4, 6, and 8 are protein profiles from uninduced bacterial cultures while lanes 3, 5, 7, and 9 are from IPTG-induced bacterial cultures. Lanes 2 and 3 are vector-control; lanes 4 and 5 are the recombinant leukotoxin molecule; lanes 6 and 7 are leukotoxin-VIP (V2 derivative—SEQ ID NO:20) fusion protein; lanes 8 and 9 are leukotoxin (full length VIP—SEQ ID NO:3) fusion protein.

These results show that *E. coli* transformed with the above-mentioned constructs, once induced with IPTG, do produce the recombinant proteins which all migrate at the expected rate of approximately 55 kDa. Compare the control recombinant leukotoxin molecule (lane 5), the leukotoxin-V2 fusion protein (lane 7), and the leukotoxin-VIP fusion protein (lane 9).

WESTERN BLOT ASSAY: The working solutions required are as follows:

(1) 5× gel running buffer (pH 8.3): 15 g of Tris, 72 g of Glycine, and 5 g of SDS are dissolved in 1 liter of dH$_2$O.

(2) Transfer buffer: 400 ml of 5× gel running buffer, 400 ml of methanol, and 1200 ml of dH$_2$O are mixed together.

(3) Tris buffer saline ("TBS"): contains 20 mM Tris and 500 mM NaCl, and pH is adjusted to 7.5 with concentrated HCl.

(4) Tris buffer saline with Tween ("TTBS"): contains 0.05% Tween 20 in TBS.

(5) Blocking solution: 1% Bovine serum albumin ("BSA") in TBS.

(6) Alkaline Phosphatase ("AP") buffer: contains 100 mM NaCl, 5 mM MgCl$_2$, and 100 mM Tris; pH is adjusted to 9.5 with HCl.

(7) AP stop buffer: contains 10 ml of 1M Tris-HCl pH 7.5 and 10 ml of 0.25 M EDTA pH 8.0. The final volume is adjusted to 500 ml with dH$_2$O;

(8) 50 mg/ml Nitro Blue Tetrazolium ("NBT"): 100 mg of NBT is dissolved in 2 ml of 70% dimethylformamide.

(9) 50 mg/ml 5-Bromo-4-Chloro-3-Indolyl-Phosphate ("BCIP"): 100 mg of BCIP is dissolved in 2 ml of 100% dimethylformamide.

The method comprises running a SDS-PAGE gel as described above for SDS-PAGE minigel. A Whatman paper and a nitrocellulose membrane are then wetted in transfer buffer for 15–30 min. The unstained gel is incubated in 20–30 ml of transfer buffer on a shaker (50 rpm) for approximately 5 to 10 min. Transfer sandwiches are then assembled: Black electrode=negative, Black half of the plastic cassette, Sponge pad, Whatman filter paper, SDS-PAGE GEL, Nitrocellulose membrane, Whatman filter paper, Sponge pad, White half of the plastic cassette, Red electrode=positive. Transfer for 1 to 1.5 hours at 200–300 mA. The sandwiches are then taken apart and the prestained marker is checked and the gel is stained as usual to determine whether the transfer is complete. The nitrocellulose membrane is washed in two changes of TBS of 5 min each and is then blocked with blocking solution (1% BSA in TBS) for 1 hour on the shaker at room temperature (or at 4–8° C. overnight). The blocking solution is discarded, then approximately 10 to 20 ml of blocking solution containing a 1/100 to 1/2000 dilution of primary antibody (according to the titre) is added to the nitrocellulose membrane which is then incubated at room temperature with shaking for 1 hour (or at 4–8° C. overnight). The antibody solution is discarded and the membrane washed twice with TTBS for 5 min each time. 20 ml of blocking solution containing a 1/2000 dilution of phosphatase-labelled anti-IgG antibody is added to the membrane and incubated at room temperature for 1 hour with shaking (or at 4–8° C. overnight). The blocking solution is discarded and the membrane washed twice with TTBS for 5 min each time. The membrane is then washed once with AP buffer for 5 min. The membrane is developed with 10 ml of AP buffer containing 66 µl of 50 mg/ml NBT and 33 µl of 50 mg/ml BCIP, and incubated at room temperature until it reaches the desired band intensity. The reaction is then stopped by incubating the membrane with AP stop buffer. The membrane is finally dried at room temperature.

The example illustrated in FIG. 5 demonstrates the immunoreactivity of a fusion protein comprising (1) VIP (SEQ ID NO:3) or a peptide derived from VIP, namely V2 (SEQ ID NO:20), and (2) a carrier molecule, namely leukotoxin. *E. coli* were transformed with the above-mentioned constructs, lysates of the cells were prepared and subjected to Western blotting as described above.

Frame B of FIG. 5 illustrates the results of this experiment. The primary antibody was raised in rabbit to a VIP-KLH (Vasoactive Intestinal Peptide—Keyhole Limpet Hemocyanin) conjugate. The second layer was a goat anti-rabbit alkaline-phosphatase labelled antibody. The lanes are as described for Frame A above with respect to SDS-PAGE minigels. The immunoreactive recombinant proteins migrate at the expected rate i.e. approximately 55 kDa. The apparently immunoreactive proteins at 85 and 35 kDa are believed to result either from non-specific reactions or be due to FcR-like (Fragment-crystalline Receptor—like) behaviour. These non-specific reactions are observed with most *E. coli* lysates tested with most antisera that were used.

These results show that the leukotoxin-V2 fusion protein (lane 7) and the leukotoxin-VIP fusion protein (lane 9) produced by IPTG-induced transformed *E. coli* both react specifically with an anti-VIP antibody.

Animal Model Development: The above-mentioned fusion proteins are initially tested in mice for their ability to elicit anti-VIP antibody as determined in radioimmunoassay. Vaccine candidates are then similarly tested in commercial fowl and finally in a food/egg production setting.

In one embodiment of the invention, a Nucleotide sequence resulting from the above preparation techniques is injected into, for example, the skeletal breast muscle of a turkey. The muscle cells in the turkey take up the exogenous DNA and effect expression of the encoded peptides derived from VIP or a cross-reactive peptide such as PACAP. The turkey, as a result, will be immunized against the biological effect of VIP and therefore exhibit modified egg production.

In yet a further embodiment of the invention, food-producing animals such as beef cattle may be immunized against VIP in a similar fashion, resulting in increased feed efficiency and weight gain.

The following example describes the injection of the recombinant peptides resulting from the above preparation techniques into the necks of turkeys, thereby immunizing them against VIP.

Eighty turkey hens (eight groups comprising ten hens each) at 16 weeks of age, were injected subcutaneously in the neck at week 0 and week 3 with 100 $\mu$g of antigen. Serum was collected from the wing vein of each bird at weeks 0, 3 and 4. The serum was subjected to radioimmunoassay (RIA) for the presence of anti-VIP antibody.

Eight different antigens were tested. The antigens injected in treatment groups 1 through 4 consisted of the multimer recombinant peptides SLV2, SLV3, SLV4, and SLP1 described earlier and illustrated in FIG. 3. The antigen injected in treatment group 5 is composed of four full length copies of vasoactive intestinal peptide and a 52 kDa carrier protein, leukotoxin. The antigen in treatment group 6 is composed of the carrier protein, leukotoxin, without any VIP linked via peptide bonds. The antigen in treatment group 7 is composed of VIP chemically conjugated to keyhole limpet hemocyanin (KLH), i.e. not cloned and synthesized as a fusion protein in the same way as the VIP-Lkt fusion product in treatment group 5. The antigen in treatment group 8 is KLH as a control against group 7.

The VIP and PACAP (the hormones) used in the antigens is radioactively labelled by the Chloroamine T method. 1 mCi (10 $\mu$l) $^{125}$Iodine (Amersham IMS.30) is added to 3 $\mu$g of the hormone dissolved in 25 $\mu$l $PO_4$ buffer. 10 $\mu$l of Chloramine T (2 mg/ml dissolved with sodium metabisulphite (0.4 mg/ml) and potassium iodide (10.0 mg/ml) in 0.05M $PO_4$ buffer is added. The reaction is terminated after exactly 15 seconds by adding 100 $\mu$l of sodium metabisulphite. The mono-iodinated fractions are isolated on a QAE Sephadex A25 column (Pharmacia).

The iodinated hormone is used in a radioimmunoassay (RIA) to calculate the amount of VIP or PACAP hormone bound to antibody in the serum samples. The antigens are formulated with 1% thimerosal (to yield 1% final volume) and sterile saline to obtain the desired amount of vaccine having the desired concentration of antigen.

The RIA results are summarized in Table 4. With respect to each treatment group, titres of anti-VIP antibodies were calculated. Binding of antigen measured in serum samples is generally considered significant if above 10%. The mean percentage of antigen binding above 10% is given in Table 4. These calculations are based on the analysis of serum samples from those birds which responded to the treatment antigen in each case. The number of birds responding to each treatment by antigen binding greater than 10% are also indicated. The antigen comprising KLH chemically conjugated with VIP provides an expected high rate of antibody response. Antigens consisting solely of KLH or Lkt elicited no antibody response, as expected. Antigens comprising VIP, multimeric fragments of VIP, or PACAP (which has a structural homology with VIP) elicited a significant response.

TABLE 4

| | | In vivo radioimmunoassay results | | |
| | | mean % binding/responders, n = 10 | | |
| Treatment | Antigen | Week 0 | Week 3 | Week 4 |
| --- | --- | --- | --- | --- |
| 1 | SLV2 | <10/0 | <10/0 | 16.5/4 |
| 2 | SLV3 | <10/0 | <10/0 | 22.8/9 |
| 3 | SLV4 | <10/0 | <10/0 | 12.8/4 |
| 4 | SLP1 | <10/0 | <10/0 | 25.4/8 |
| 5 | SLF4 | <10/0 | <10/0 | 12.6/2 |
| 6 | LKT | <10/0 | <10/0 | <10/0 |
| 7 | KLH-VIP | <10/0 | <10/0 | 55.6/10 |
| 8 | KLH | <10/0 | <10/0 | <10/0 |

We claim:

1. An isolated protein comprising: (1) at least one peptide having at least 6 contiguous amino acids of (a) a vasoactive intestinal peptide (VIP) or (b) a pituitary adenylate cyclase activating protein (PACAP), but less than the full-length of VIP or PACAP, and (2) a carrier molecule that enhances the immunogenicity of the peptide, wherein said carrier molecule is a 52 kDa leukotoxin molecule, wherein said protein elicits the production of antibodies which neutralize vasoactive intestinal peptide in vivo.

2. The protein according to claim 1 wherein the protein comprises vasoactive intestinal peptide isolated from more than one animal species.

3. A method of immunizing an egg-laying bird against vasoactive intestinal peptide comprising treating the bird with the protein according to claim 1.

4. The method according to claim 3 wherein the bird is turkey.

5. A method of immunizing a food-producing animal against vasoactive intestinal peptide comprising treating the animal with the protein according to claim 1.

6. The protein according to claim 1 wherein the at least one peptide is tandemly repeated.

7. The protein according to claim 1 wherein the peptide is from a sequence selected from the group consisting of SEQ ID NO:15, SEQ ID NO;16, SEQ ID NO:17, SEQ ID NO:18, SEQ ID NO:19, SEQ ID NO:20, SEQ ID NO:21, SEQ ID NO:22 and SEQ ID NO:23.

8. The protein according to claim 7 wherein the peptide is SEQ ID NO:20.

9. A method of immunizing an egg-laying bird against vasoactive intestinal peptide comprising treating the bird with the protein according to claim 7.

10. A method of immunizing a food-producing animal against vasoactive intestinal peptide comprising treating the animal with the protein according to claim 7.

11. An isolated nucleic acid molecule which encodes a recombinant protein comprising (1) at least one peptide having at least 6 contiguous amino acids of (a) a vasoactive intestinal peptide (VIP), or (b) a pituitary adenylate cyclase activating protein (PACAP), but less than the full-length of VIP or PACAP, and (2) a carrier molecule that enhances the immunogenicity of the peptide, wherein said carrier molecule is a 52 kDa leukotoxin molecule, wherein said recombinant protein elicits the production of antibodies which neutralize vasoactive intestinal peptide in vivo.

12. An expression cassette comprising (1) a first nucleic acid molecule according to claim 11, and (2) additional nucleotide sequences operably linked to the first nucleic acid molecule which control the transcription and translation of the first nucleotide sequence in a host cell.

13. A host cell stably transformed by the expression cassette of claim 12.

14. A method of producing a recombinant protein comprising growing a population of host cells according to claim 13 under conditions whereby the expression cassette is expressed.

15. The nucleic acid molecule according to claim 11 wherein the at least one peptide is tandemly repeated in the recombinant protein encoded by the nucleic acid molecule.

16. The nucleic acid molecule according to claim 11 wherein the nucleic acid molecule encodes VIP peptides isolated from more than one animal species.

17. The nucleic acid molecule according to claim 11 wherein the nucleic acid molecule encodes a peptide from a sequence selected from the group consisting of SEQ ID NO:15, SEQ ID NO:16, SEQ ID NO:17, SEQ ID NO:18, SEQ ID NO:19, SEQ ID NO;20, SEQ ID NO:21, SEQ ID NO:22 and SEQ ID NO:23.

18. The nucleic acid molecule according to claim 17 wherein the peptide encoded by the nucleic acid molecule is SEQ ID NO:20.

* * * * *

UNITED STATES PATENT AND TRADEMARK OFFICE
CERTIFICATE OF CORRECTION

PATENT NO. : 6,037,321
DATED : March 14, 2000
INVENTOR(S) : Cox et al.

It is certified that error appears in the above-identified patent and that said Letters Patent is hereby corrected as shown below:

In column 2, line 53, please replace "©" with --(c)--.

Signed and Sealed this

Twenty-fourth Day of April, 2001

Attest:

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
    (A) LENGTH: 28 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 1:

```
His Ser Asp Ala Val Phe Thr Asp Asn Tyr Ser Arg Phe Arg Lys Gln
 1               5                  10                  15

Met Ala Val Lys Lys Tyr Leu Asn Ser Val Leu Thr
                20                  25
```

(2) INFORMATION FOR SEQ ID NO: 2:

(i) SEQUENCE CHARACTERISTICS:
    (A) LENGTH: 28 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 2:

```
His Ser Asp Ala Ile Phe Thr Gln Gln Tyr Ser Lys Leu Leu Ala Lys
 1               5                  10                  15

Leu Ala Leu Gln Lys Tyr Leu Ala Ser Ile Leu Gly
                20                  25
```

(2) INFORMATION FOR SEQ ID NO: 3:

(i) SEQUENCE CHARACTERISTICS:
    (A) LENGTH: 28 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 3:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO: 4:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 4:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO: 5:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 5:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO: 6:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 6:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO: 7:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 7:

```
His Ser Asp Ala Val Phe Thr Asp Asn Tyr Ser Arg Ile Arg Lys Gln
1               5                   10                  15

Met Ala Val Lys Lys Tyr Ile Asn Ser Leu Leu Ala
            20                  25
```

(2) INFORMATION FOR SEQ ID NO: 8:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 8:

```
His Ser Asp Ala Val Phe Thr Asp Asn Tyr Ser Arg Phe Arg Lys Gln
1               5                   10                  15

Met Ala Ala Lys Lys Tyr Leu Asn Ser
            20                  25
```

(2) INFORMATION FOR SEQ ID NO: 9:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 9:

```
His Ser Asp Ala Val Phe Thr Asp Ser Tyr Thr Arg Leu Leu Lys Gln
1               5                   10                  15

Met Ala Met Arg Lys Tyr Leu Asp Ser Ile Leu Asn
            20                  25
```

(2) INFORMATION FOR SEQ ID NO: 10:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 10:

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25
```

(2) INFORMATION FOR SEQ ID NO: 11:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 11:

```
His Ser Asp Ala Val Phe Thr Asp Asn Tyr Thr Arg Leu Arg Lys Gln
1               5                   10                  15
```

```
Met Ala Val Lys Lys Tyr Leu Asn Ser Ile Leu Asn
            20                  25

(2) INFORMATION FOR SEQ ID NO: 12:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 12:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO: 13:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 13:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO: 14:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 14:

His Ser Asp Ala Leu Phe Thr Asp Thr Tyr Thr Arg Leu Arg Lys Gln
1               5                   10                  15

Met Ala Met Lys Lys Tyr Leu Asn Ser Val Leu Asn
            20                  25

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO: 15:

His Ser Asp Ala Val Phe Thr Asp Asn Tyr
1               5                   10
```

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: protein (v) FRAGMENT TYPE: internal (xi) SEQUENCE DESCRIPTION: SEQ ID NO: 16:

```
Thr Asp Asn Tyr Thr Arg Leu Arg Lys Gln
1               5                   10
```

(2) INFORMATION FOR SEQ ID NO: 17:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: protein (v) FRAGMENT TYPE: internal (xi) SEQUENCE DESCRIPTION: SEQ ID NO: 17:

```
Leu Arg Lys Gln Met Ala Val Lys Lys Tyr
1               5                   10
```

(2) INFORMATION FOR SEQ ID NO: 18:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: protein (v) FRAGMENT TYPE: C-terminal (xi) SEQUENCE DESCRIPTION: SEQ ID NO: 18:

```
Val Lys Lys Tyr Leu Asn Ser Ile Leu Asn
1               5                   10
```

(2) INFORMATION FOR SEQ ID NO: 19:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO: 19:

```
His Ser Asp Ala Val Phe Thr Asp Asn Tyr Thr Arg
1               5                   10
```

(2) INFORMATION FOR SEQ ID NO: 20:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (v) FRAGMENT TYPE: internal (xi) SEQUENCE DESCRIPTION: SEQ ID NO: 20:

Phe Thr Asp Asn Tyr Thr Arg Leu Arg Lys Gln Met
1               5                   10

(2) INFORMATION FOR SEQ ID NO: 21:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: protein (v) FRAGMENT TYPE: internal (xi) SEQUENCE DESCRIPTION: SEQ ID NO: 21:

Thr Arg Leu Arg Lys Gln Met Ala Val Lys Lys Tyr Leu
1               5                   10

(2) INFORMATION FOR SEQ ID NO: 22:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: protein (v) FRAGMENT TYPE: C-terminal (xi) SEQUENCE DESCRIPTION: SEQ ID NO: 22:

Met Ala Val Lys Lys Tyr Leu Asn Ser Ile Leu Asn
1               5                   10

(2) INFORMATION FOR SEQ ID NO: 23:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: protein (v) FRAGMENT TYPE: internal (xi) SEQUENCE DESCRIPTION: SEQ ID NO: 23:

Ser Arg Tyr Arg Lys Gln Met Ala Val Lys Lys Tyr Leu Ala
1               5                   10

(2) INFORMATION FOR SEQ ID NO: 24:

(i) SEQUENCE CHARACTERISTICS:
            (A) LENGTH: 150 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 24:

GATCTCATAG CGATGCGGTG TTTACCGATA ACTATACCCG TCATAGCGAT GCGGTGTTTA      60

CCGATAACTA TACCCGTCAT AGCGATGCGG TGTTTACCGA TAACTATACC CGTCATAGCG    120

ATGCGGTGTT TACCGATAAC TATACCCGTG                                    150

(2) INFORMATION FOR SEQ ID NO: 25:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 25:

GATCCACGGG TATAGTTATC GGTAAACACC GCATCGCTAT GACGGGTATA GTTATCGGTA    60

AACACCGCAT CGCTATGACG GGTATAGTTA TCGGTAAACA CCGCATCGCT ATGACGGGTA   120

TAGTTATCGG TAAACACCGC ATCGCTATGA                                   150

(2) INFORMATION FOR SEQ ID NO: 26:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 26:

GATCTTTTAC CGATAACTAT ACCCGTCTGC GTAAACAGAT GTTTACCGAT AACTATACCC    60

GTCTGCGTAA ACAGATGTTT ACCGATAACT ATACCCGTCT GCGTAAACAG ATGTTTACCG   120

ATAACTATAC CCGTCTGCGT AAACAGATGG                                   150

(2) INFORMATION FOR SEQ ID NO: 27:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 27:

GATCCCATCT GTTTACGCAG ACGGGTATAG TTATCGGTAA ACATCTGTTT ACGCAGACGG    60

GTATAGTTAT CGGTAAACAT CTGTTTACGC AGACGGGTAT AGTTATCGGT AAACATCTGT   120

TTACGCAGAC GGGTATAGTT ATCGGTAAAA                                   150

(2) INFORMATION FOR SEQ ID NO: 28:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 28:

GATCTACCCG TCTGCGTAAA CAGATGGCGG TGAAAAAATA TCTGACCCGT CTGCGTAAAC    60

AGATGGCGGT GAAAAAATAT CTGACCCGTC TGCGTAAACA GATGGCGGTG AAAAAATATC   120

TGACCCGTCT GCGTAAACAG ATGGCGGTGA AAAAATATCT GG                     162

(2) INFORMATION FOR SEQ ID NO: 29:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 29:

```
GATCCCAGAT ATTTTTTCAC CGCCATCTGT TTACGCAGAC GGGTCAGATA TTTTTTCACC        60
GCCATCTGTT TACGCAGACG GGTCAGATAT TTTTTCACCG CCATCTGTTT ACGCAGACGG       120
GTCAGATATT TTTTCACCGC CATCTGTTTA CGCAGACGGG TA                          162
```

(2) INFORMATION FOR SEQ ID NO: 30:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 30:

```
GATCTATGGC GGTGAAAAAA TATCTGAACA GCATTCTGAA CATGGCGGTG AAAAAATATC        60
TGAACAGCAT TCTGAACATG GCGGTGAAAA AATATCTGAA CAGCATTCTG AACATGGCGG       120
TGAAAAAATA TCTGAACAGC ATTCTGAACG                                        150
```

(2) INFORMATION FOR SEQ ID NO: 31:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 31:

```
GATCCGTTCA GAATGCTGTT CAGATATTTT TTCACCGCCA TGTTCAGAAT GCTGTTCAGA        60
TATTTTTTCA CCGCCATGTT CAGAATGCTG TTCAGATATT TTTTCACCGC CATGTTCAGA       120
ATGCTGTTCA GATATTTTTT CACCGCCATA                                        150
```

(2) INFORMATION FOR SEQ ID NO: 32:

(i) SEQUENCE CHARACTERISTICS:
        (A) LENGTH: 174 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 32:

```
GATCTAGCCG TTATCGTAAA CAGATGGCGG TGAAAAAATA TCTGGCGAGC CGTTATCGTA        60
AACAGATGGC GGTGAAAAAA TATCTGGCGA GCCGTTATCG TAAACAGATG GCGGTGAAAA       120
AATATCTGGC GAGCCGTTAT CGTAAACAGA TGGCGGTGAA AAAATATCTG GCGG             174
```

(2) INFORMATION FOR SEQ ID NO: 33:

(i) SEQUENCE CHARACTERISTICS:
            (A) LENGTH: 174 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 33:

GATCCCGCCA GATATTTTTT CACCGCCATC TGTTTACGAT AACGGCTCGC CAGATATTTT        60

TTCACCGCCA TCTGTTTACG ATAACGGCTC GCCAGATATT TTTTCACCGC CATCTGTTTA       120

CGATAACGGC TCGCCAGATA TTTTTTCACC GCCATCTGTT TACGATAACG GCTA             174

(2) INFORMATION FOR SEQ ID NO: 34:

(i) SEQUENCE CHARACTERISTICS:
            (A) LENGTH: 90 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 34:

GATCTAGCCG TTATCGTAAA CAGATGGCGG TGAAAAAATA TCTGGCGAGC CGTTATCGTA        60

AACAGATGGC GGTGAAAAAA TATCTGGCGG                                        90

(2) INFORMATION FOR SEQ ID NO: 35:

(i) SEQUENCE CHARACTERISTICS:
            (A) LENGTH: 90 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 35:

GATCCCGCCA GATATTTTTT CACCGCCATC TGTTTACGAT AACGGCTCGC CAGATATTTT        60

TTCACCGCCA TCTGTTTACG ATAACGGCTA                                        90

(2) INFORMATION FOR SEQ ID NO: 36:

(i) SEQUENCE CHARACTERISTICS:
            (A) LENGTH: 78 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 36:

GATCTTTTAC CGATAACTAT ACCCGTCTGC GTAAACAGAT GTTTACCGAT AACTATACCC        60

GTCTGCGTAA ACAGATGG                                                     78

(2) INFORMATION FOR SEQ ID NO: 37:

(i) SEQUENCE CHARACTERISTICS:
            (A) LENGTH: 78 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 37:

GATCCCATCT GTTTACGCAG ACGGGTATAG TTATCGGTAA ACATCTGTTT ACGCAGACGG    60

GTATAGTTAT CGGTAAAA                                                 78

(2) INFORMATION FOR SEQ ID NO: 38:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 38:

GATCTACCCG TCTGCGTAAA CAGATGGCGG TGAAAAAATA TCTGACCCGT CTGCGTAAAC    60

AGATGGCGGT GAAAAAATAT CTGG                                          84

(2) INFORMATION FOR SEQ ID NO: 39:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 39:

GATCCCAGAT ATTTTTTCAC CGCCATCTGT TTACGCAGAC GGGTCAGATA TTTTTTCACC    60

GCCATCTGTT TACGCAGACG GGTA                                          84

(2) INFORMATION FOR SEQ ID NO: 40:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 40:

GATCTATGGC GGTGAAAAAA TATCTGAACA GCATTCTGAA CATGGCGGTG AAAAAATATC    60

TGAACAGCAT TCTGAACG                                                 78

(2) INFORMATION FOR SEQ ID NO: 41:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 41:

GATCCGTTCA GAATGCTGTT CAGATATTTT TTCACCGCCA TGTTCAGAAT GCTGTTCAGA    60

TATTTTTTCA CCGCCATA                                                 78

(2) INFORMATION FOR SEQ ID NO: 42:

(i) SEQUENCE CHARACTERISTICS:
        (A) LENGTH: 78 base pairs

-continued

```
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 42:

GATCTCATAG CGATGCGGTG TTTACCGATA ACTATACCCG TCATAGCGAT GCGGTGTTTA     60

CCGATAACTA TACCCGTG                                                   78

(2) INFORMATION FOR SEQ ID NO: 43:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 43:

GATCCACGGG TATAGTTATC GGTAAACACC GCATCGCTAT GACGGGTATA GTTATCGGTA     60

AACACCGCAT CGCTATGA                                                   78
```